US007862523B2

(12) United States Patent
Ruotoistenmaki

(10) Patent No.: US 7,862,523 B2
(45) Date of Patent: Jan. 4, 2011

(54) FORCE OR PRESSURE SENSOR AND METHOD FOR APPLYING THE SAME

(75) Inventor: Heikki Ruotoistenmaki, Espoo (FI)

(73) Assignee: Finsor Oy, Espoo (FI)

( * ) Notice: Subject to any disclaimer, the term of this patent is extended or adjusted under 35 U.S.C. 154(b) by 6 days.

(21) Appl. No.: 12/076,399

(22) Filed: Mar. 18, 2008

(65) Prior Publication Data

US 2008/0167561 A1 Jul. 10, 2008

Related U.S. Application Data

(62) Division of application No. 10/525,703, filed as application No. PCT/FI2003/000604 on Aug. 15, 2003, now Pat. No. 7,726,209.

(30) Foreign Application Priority Data

Aug. 21, 2002 (FI) ................................. 20021508

(51) Int. Cl.
A61B 5/11 (2006.01)

(52) U.S. Cl. ...................... 600/595; 600/484; 600/527; 600/537

(58) Field of Classification Search ................. 600/595, 600/534, 535, 527
See application file for complete search history.

(56) References Cited

U.S. PATENT DOCUMENTS

| 4,320,766 A | * | 3/1982 | Alihanka et al. ............. 600/484 |
| 4,657,026 A | * | 4/1987 | Tagg .......................... 600/534 |
| 5,148,706 A | * | 9/1992 | Masuda et al. ................ 73/172 |
| 5,583,295 A | | 12/1996 | Nagase et al. |
| 5,590,650 A | * | 1/1997 | Genova ....................... 600/301 |
| 5,964,720 A | | 10/1999 | Pelz |
| 6,547,743 B2 | * | 4/2003 | Brydon ....................... 600/534 |
| 6,840,907 B1 | * | 1/2005 | Brydon ....................... 600/534 |
| 2002/0100330 A1 | * | 8/2002 | Eickhoff et al. ............... 73/715 |
| 2004/0000195 A1 | * | 1/2004 | Yanai et al. ................... 73/717 |

FOREIGN PATENT DOCUMENTS

| EP | 0 055 345 | | 7/1982 |
| WO | WO-0164103 A1 | * | 9/2001 |
| WO | WO 0231461 | | 4/2002 |

OTHER PUBLICATIONS

International Search Report for PCT/FI03/00604 dated Nov. 21, 2004.

* cited by examiner

*Primary Examiner*—Max Hindenburg
*Assistant Examiner*—Michael C Stout
(74) *Attorney, Agent, or Firm*—Buchanan Ingersoll & Rooney PC

(57) ABSTRACT

The invention relates to a force or pressure sensor and a method for applying the same. The pressure sensor includes a substantially rigid, mechanical-load resistant frame, a flexible diaphragm secured over its peripheral rim to the frame, and a piezoelectric sensor diaphragm applied to the surface of the flexible diaphragm. The sensor diaphragm loading element comprises a substantially rigid, mechanical-load resistant cover, having its protrusion or shoulder bearing against a middle section of the flexible diaphragm and thereby prestressing the flexible diaphragm and the piezoelectric sensor diaphragm attached thereto. The frame and the cover define therebetween a closed, hermetically sealed housing chamber, the flexible diaphragm and the piezoelectric sensor diaphragm located thereinside. The placement of one or more responsive, yet load-resistant sensors in contact with a bed enables measuring a sleeping or lying person for his or her heart rate and respiratory amplitude, as well as frequency.

6 Claims, 2 Drawing Sheets

FORCE OR PRESSURE SENSOR AND METHOD FOR APPLYING THE SAME

REFERENCE TO RELATED APPLICATION

This application is a divisional of application Ser. No. 10/525,703, filed Feb. 18, 2005, pending, which is a national stage of PCT/FI03/00604, filed Aug. 15, 2003, the disclosure of which is incorporated herein by reference.

BACKGROUND OF THE INVENTION

The invention relates to a force or pressure sensor, comprising a substantially rigid, mechanical-load resistant frame, a flexible diaphragm secured over its peripheral rim to the frame, and a piezoelectric sensor diaphragm applied to the surface of the flexible diaphragm.

The invention relates also to a method for applying this method, such that a sleeping or lying person can be measured for his or her heart rate and respiratory amplitude, as well as frequency.

Patent publications U.S. Pat. Nos. 4,570,097, 4,567,395, 4,590,400 and 5,353,633 disclose a piezoelectric pressure sensor for measuring changes of a cylinder pressure in an internal combustion engine during ignition. The cylinder pressure is supplied by means of a separate transmitter body to a piezoelement, which is subjected to compression according to a pressure change occurring in the engine cylinder. Since the piezocrystal is compressed and its surface area is relatively small, the sensor remains comparatively low in responsivity. The sensor is not structurally designed to provide simultaneously a high load rating and a high sensitivity.

Published application WO 99/47044 discloses a piezoelectric pressure sensor for measuring blood pressure changes in a blood vessel. The pulse of a blood vessel is delivered by means of a transmitter diaphragm and a rod to a piezoelement, which is subjected to deflection according to a pressure change occurring in the blood vessel. Since the load is received by a sensitive transmitter diaphragm, the sensor has a remarkably low static resistance to pressure. In addition, the sensor's piezoelement is structurally asymmetrical.

Patent publication U.S. Pat. No. 5,365,937 describes a piezoelectric sensor for measuring cardiomuscular rate on skin surface. Some of the sensor's housing structure consists of a piezoelement. Since some of the sensor's housing structure consists of a piezoelement, the sensor's static resistance to pressure is relatively modest. The movement applied to a piezoelement in the sensor is transmitted over the entire surface area of the piezoelement.

Patent publication U.S. Pat. No. 4,803,671 discloses a sensor for acoustic pressure wave pulses, wherein a piezoelectric measuring diaphragm is disposed in a space between two coupling diaphragms filled with a coupling medium. This sensor is not capable of handling major external loads, either.

SUMMARY OF THE INVENTION

It is an object of the invention to provide a force or pressure sensor, which is highly capable of handling major external loads, yet at the same time is extremely responsive even to very slight changes in force or pressure.

This object is achieved by a force or pressure sensor of the invention, which is provided with the characterizing features set forth in the appended claim 1. The dependent claims disclose preferred structural solutions of the invention, which assist in reaching the above objective.

By virtue of the features of a sensor of the invention, i.e. a high load rating and responsivity, it can be applied with particular benefits in a method, by which a sleeping or lying person is measured for his or her heart rate and respiratory amplitude, as well as frequency. The features characteristic of the method are set forth in the appended claim 12. Implementing options for the method are set forth in claims 13 and 14.

BRIEF DESCRIPTION OF THE DRAWINGS

The inventive force or pressure sensor and its application will now be described in more detail with reference to the accompanying drawings, in which.

DETAILED DESCRIPTION OF THE PREFERRED EMBODIMENTS

Figure 1:
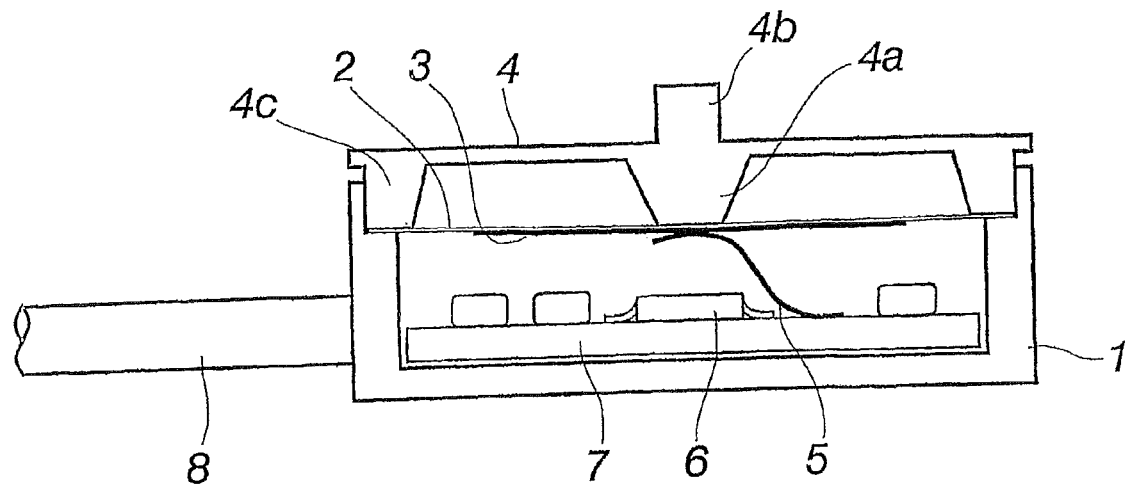
FIG. 1 shows a force or pressure sensor of the invention in a sectional view.

The sensor to be described hereinafter has properties like a high resistance to force or pressure, a high sensitivity, a trouble-free operation, a simplicity of required electronics, and a broad frequency repetition. Surprisingly, all these qualities are achieved with a sensor assembly to be described hereinbelow.

A sensor frame 1 is substantially rigid and resistant to mechanical loading. Therefore, the frame 1 is made e.g. from stainless steel. A sensor cover 4 is also substantially rigid and resistant to mechanical loading, and preferably made from stainless steel or another suitable metal. The frame 1 and the cover 4 are metal blocks in the shape of bodies of revolution. They can also be made of a plastic or composite material or some other rigid, durable material. The actual sensor element comprises a piezoelectric ceramic diaphragm 3, which is applied to a thin, flexible metal diaphragm 2. The flexible metal diaphragm is in turn attached by its peripheral rim between the frame 1 and the cover 2. The frame 1 and the cover 2 define therebetween a closed, hermetically sealed housing chamber, the flexible diaphragm 2 and the sensor diaphragm 3 being located thereinside.

In terms of its diameter, the piezoceramic sensor diaphragm 3 is smaller than the metal diaphragm 2, which is why the sensor diaphragm 3 has its peripheral rims left at a distance from the inner periphery of the housing chamber. Such combination of a metal diaphragm and a piezoceramic sensor diaphragm is prior known and generally used in piezoelectric loudspeakers for producing sound by conducting an electric signal to the diaphragm. Such a piezoelectric loudspeaker is prior known e.g. from patent publication US-2002/0067840A1.

The cover 4, functioning as a loading element, is provided with a protrusion or shoulder 4a, bearing against the flexible diaphragm 2 in its mid-section, and hence prestressing the flexible diaphragm 2 and the sensor diaphragm 3 attached thereto. A sensor-signal transmitting contact spring 5 is in contact with the sensor diaphragm 3 opposite to the cover protrusion 4a. The frame 1, the cover 4, and the diaphragms 2 and 3 are all rotationally symmetrical with respect to the cover protrusion or shoulder 4a. Despite the fact that the cover has a load rating or load carrying capacity which is very high, typically more than 50 kg and preferably more than 100 kg, the sensor has an extremely high responsivity to changes in a force F or a pressure p. It has been discovered in practical experiments that the sensor provides a clear and highly decipherable output signal as the change of a load applied to the cover 4 is less than $10^{-6}$, even less than $10^{-9}$ times.load rating of the cover 4. In this conjunction, the load rating of the cover refers to its elastic loading section, over which the sensor retains its functionality and high responsivity.

An amplifier 6 and its circuit board 7 are located within the housing chamber defined by the frame 1 and the cover 4. The amplifier 6 has its input impedance matched to provide a desired settling time, during which the amplifier's 6 output sets essentially to zero as the loading applied to the cover 4 remains unchanged. Thus, the input impedance of the amplifier 6 is used for making the sensor applicable to various applications, in which the measured fluctuation of force or pressure can happen at a low or a high frequency. The sensor's output cable 8, extending from the amplifier 6, comprises a single- or multi-wire screened cable.

Figure 2:
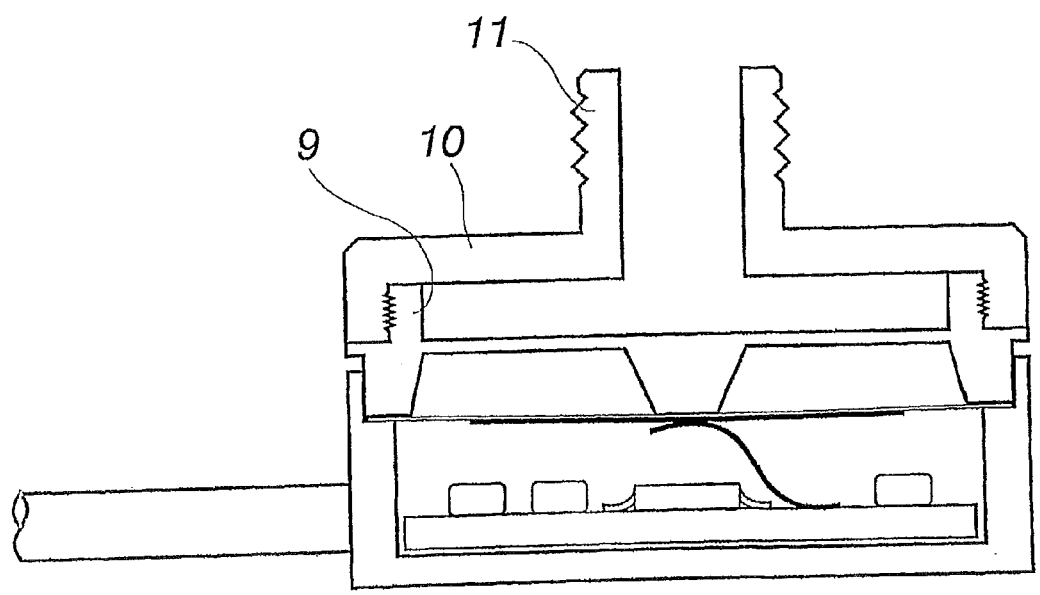
FIG. 2 shows a variant for the sensor of FIG. 1, which can be used for measuring changes in fluid or gas pressure.

FIG. 2 differs from the embodiment of FIG. 1 in that the cover 4 has its threaded sleeve 9 fitted with an adapter element 10, 11, by way of which the cover 4 can be loaded with changes in a fluid or gas pressure. The member 10 defines a pressure chamber, and the member 11 is e.g. a threaded fitting piece.

In the embodiment of FIG. 1, the cover 4 is also provided in the middle with an upward protrusion 4b, which is subjected to mechanical loading. The cover plate 4 has a thickness between a curb collar 4c and the central protrusions 4a, 4b in the order of e.g. 1 mm, and the sensor diameter can be in the order of 2-3 mm.

The sensor's operation is based on the fact that, as a compressive force is applied to the protruding part 4b in the mid-section of the cover plate 4, the cover element 4 depresses slightly inward and deflects the piezo-diaphragm 3 with its protrusion 4a. The deflection of the cover element 4 must be very slight indeed, as the ceramic piezo-diaphragm 3 is easily ruptured. Upon deflection, the piezo-diaphragm 3 generates a potential, which is conducted by way of the contact spring 5 to the high-impedance amplifier 6. The amplifier 6 turns the output impedance lower, thus improving the output signal's immunity to interference.

The application of a sensor of the invention will now be described in connection with a method, whereby a sleeping or lying person is measured for his or her heart rate and respiratory amplitude, as well as frequency. In the method, a sleeping person can be measured, without having any wires or transducers connected to the person, for his or her heart rate and respiration, regardless of a person's lying posture (on his or her back, side or belly). The method utilizes a ballistocardiographic signal generated by the heart and a weight change in a person at rest, resulting from pulmonary movements and strains. The measurement has been enabled by a sensor of the invention, which is concurrently provided with a high load rating and a high responsivity.

Figure 3:
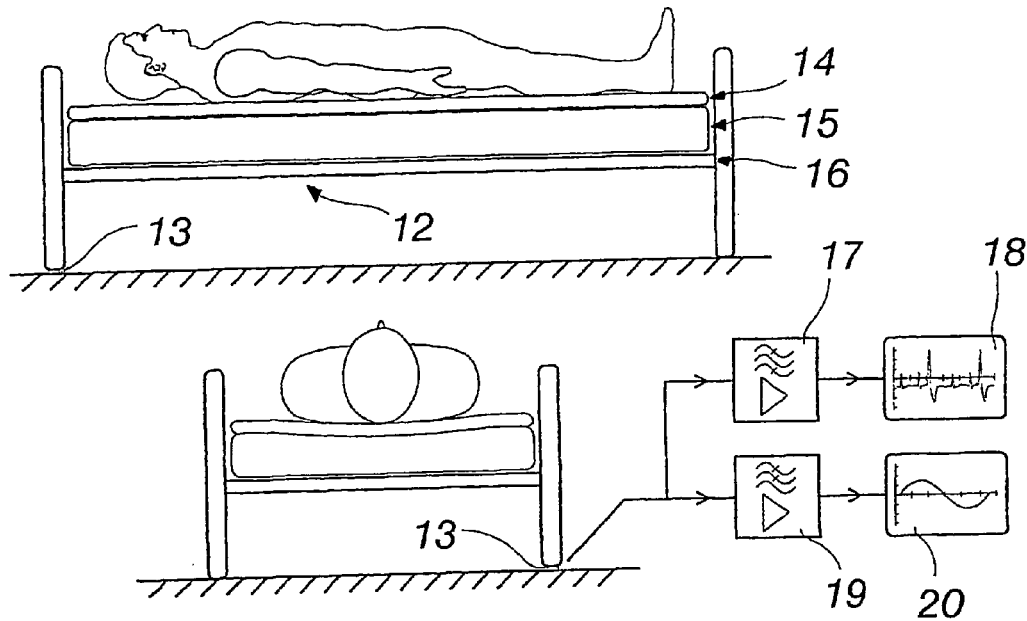
FIG. 3 depicts a sensor application method for measuring a sleeping or lying person for his or her heart rate and respiratory amplitude, as well as frequency.

FIG. 3 illustrates a first alternative of the method, wherein under the post or posts of a bed is placed a responsive sensor 13 as described above, identifying a change in force or pressure. As a person is lying, the sensor identifies, through the intermediary of a bed frame 16, a weight change caused by the heart as well as respiration. The signal processing is effected by using a filter 17 for the filter-separation of a higher-rate frequency component coming from the sensor 13, thereby enabling the measurement of a person's heart rate for its amplitude and frequency. An oscilloscope 18 is provided with a graph representative of cardiac function. By using a filter 19 for the filter-separation of a low frequency component coming from the sensor 3, it is possible to measure the amplitude as well as the frequency of human respiration, a graph representing the same being displayable on an oscilloscope 20. The oscilloscopes 18 and 20 are optionally replaceable with a plotter or an electronic memory, from which the graphs can be transferred onto a computer screen.

Figure 4:
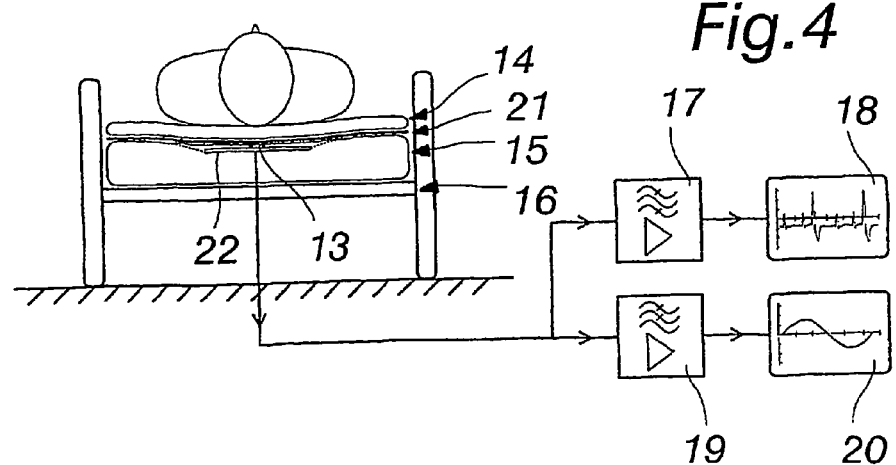
FIG. 4 shows a method otherwise similar to FIG. 3 except for an alternative disposition of the sensor.

In the alternative of FIG. 4, the sensor 13 is placed between a top mattress 14 and an actual mattress 15 in a bed 12 in line with the thorax of a person. The sensor 13 is prevented from sinking in the top mattress 14 and/or the actual mattress 15 by means of panels 21 and 22, which are more rigid than the mattresses and between which the sensor 13 is positioned. In the illustrated case, under the top mattress 14 lies a resilient panel 20, extending essentially across the width of the mattresses, and thereunder a rigid backing panel 22, whose surface area is confined within a section of the upper body, such that the function of the actual mattress 15 is not substantially impeded. By using the panels 21, 22 of an appropriate surface area, it is possible to identify the heart rate, as well as respiration, reliably over a more extensive area (and, if desired, a change in the sleeping posture of a sleeping person during sleep). Hence, the comfort of a sleeping platform is not impaired by the sensor system.

The method can be used in monitoring or attending to heart patients, lung patients, demented patients, sleep apnea patients, a child's sleep, etc.

Other possible applications for a sensor of the invention include:
  Wearing of engine bearings (audibility range)
  Pressure changes in the combustion chamber of an engine cylinder
  Dynamic stress of bearing supports (measurement at low frequencies; stresses and torques applied to axles etc.)
  Wobbling of building structures (swaying of tall buildings and smokestack structures, e.g. as a result of wind action)
  As a seismographic sensor for controlling an earthquake alarm system (apartment-specific alarm like a fire alarm)
  As a surveillance device in buildings (capable of detecting depression of floor) and
  Sensor can also be used for measuring a fluid or air pressure by modifying the cover plate design.

What is claimed is:

1. A method for using a force or pressure sensor comprising a substantially rigid, mechanical-load resistant frame, a flexible diaphragm having a peripheral rim, the flexible diaphragm being secured at the peripheral rim to the frame, and a piezoelectric sensor diaphragm applied to the surface of the flexible diaphragm, wherein the sensor diaphragm loading element comprises a substantially rigid cover capable of carrying mechanical loading of more than 50 kg, wherein the cover includes a protrusion or shoulder, bearing against a middle section of the flexible diaphragm and thus, by deflection before an external loading is applied, prestressing the flexible diaphragm and the piezoelectric sensor diaphragm attached thereto, and wherein the frame and the cover define therebetween a closed housing chamber, the flexible diaphragm and the piezoelectric sensor diaphragm being located thereinside, the method comprising the steps of:
  disposing one or more of the force or pressure sensors in contact with a bed and measuring a sleeping or lying person for his or her heart rate and respiratory amplitude.

2. The method of claim 1, wherein the measurement is implemented with one or more sensors placed under a bed post or posts.

3. The method of claim 1, wherein the measurement is implemented with one or more sensors placed in contact with a bed mattress and the sensor is prevented from sinking in the mattress with panels which are more rigid than the mattress.

4. The method of claim 1, further comprising measuring a sleeping or lying person for his or her respiratory frequency.

5. The method of claim 3, wherein the bed mattress includes a top mattress and a lower mattress, the sensor being positioned between the top mattress and the lower mattress.

6. The method of claim 1, wherein the peripheral rim of the flexible diaphragm is secured between the frame and the cover.

* * * * *